United States Patent [19]

Tsumura et al.

[11] Patent Number: 5,175,309

[45] Date of Patent: Dec. 29, 1992

[54] PREPARATION PROCESS OF N-SUBSTITUTED MALEIMIDES

[75] Inventors: Ryuichiro Tsumura, Yokohama; Kunimitsu Fukumura, Kanagawa; Teruo Muraishi, Yokohama, all of Japan

[73] Assignee: Mitsui Toatsu Chemicals Inc., Tokyo, Japan

[21] Appl. No.: 448,185

[22] Filed: Dec. 8, 1989

[30] Foreign Application Priority Data

| Dec. 9, 1988 [JP] | Japan | 63-310050 |
| Dec. 13, 1988 [JP] | Japan | 63-312951 |
| Dec. 20, 1988 [JP] | Japan | 63-319382 |
| Jan. 31, 1989 [JP] | Japan | 1-19844 |
| Feb. 8, 1989 [JP] | Japan | 1-27502 |
| Jun. 14, 1989 [JP] | Japan | 1-149514 |

[51] Int. Cl.$^5$ ............. C07D 207/452; C07D 207/444; C07D 403/06

[52] U.S. Cl. .................. 548/548; 548/545; 548/521; 548/549

[58] Field of Search ............... 548/548, 545, 549, 521

[56] References Cited

U.S. PATENT DOCUMENTS 4,786,738  11/1988  Kita et al. ............... 548/548

FOREIGN PATENT DOCUMENTS

| 0082620 | 6/1983 | European Pat. Off. ........... 548/548 |
| 51-40078 | 11/1976 | Japan . |
| 55-46394 | 11/1980 | Japan . |
| 60-11465 | 1/1985 | Japan . |
| 61-5066 | 1/1986 | Japan . |
| 61-60647 | 3/1986 | Japan . |
| 62-63562 | 3/1987 | Japan . |
| 2230766A | 10/1987 | Japan ................................. 548/548 |

OTHER PUBLICATIONS

Cava et al., N-phenylmaleimide, Organic Synthesis, vol. 41, pp. 93–95.
CA 105(12):98099y.

*Primary Examiner*—David B. Springer
*Attorney, Agent, or Firm*—Millen, White & Zelano

[57] ABSTRACT

A process for the preparation of N-substituted maleimides by conducting heat-dehydration and dehydrating imidization of N-substituted maleamic acids under azeotropic distillation of generated water in a solvent mixture containing a solvent capable of forming water azeotrope and an organic aprotic polar solvent, in the presence as catalyst of a zinc salt of a maleamic acid, metallic zinc or a zinc compound which forms a zinc salt of the N-substituted maleamic acid in the reaction system.

23 Claims, No Drawings

PREPARATION PROCESS OF N-SUBSTITUTED MALEIMIDES

BACKGROUND OF THE INVENTION

1. Field of the Invention

The present invention relates to a process for the preparation of N-substituted maleimides.

2. Prior Art of the Invention

Various processes have traditionally been employed for preparing a N-substituted maleimide. In a generally known preparation process, maleic anhydride is reacted with a primary amine and the resulting N-substituted maleamic acid is imidized by cyclodehydration.

For example, N-phenyl maleimide can be prepared by an imidizing reaction through intramolecular cyclodehydration as follows:

$$C_6H_5NHCOCH=CHCOOH \longrightarrow$$

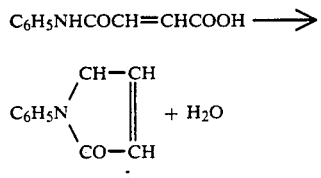 $+ H_2O$

These processes can be roughly divided into those using a dehydrating agent and those using a catalyst.

The method which uses a dehydrating agent carries out the reaction by employing an equimolar amount or more of a dehydrating agent such as acetic anhydride as disclosed, for example, in U.S. Ser. No. 244,453 or Organic Syntheses, 41, 93. The method is excellent with respect to mild reaction conditions and relatively high yield of the reaction product. However, the method requires a large amount of expensive dehydrating agent and a complex treatment for separating the product after finishing the reaction. Consequently, the method leads to high production cost of the maleimide and is unsuitable for commercial production.

The dehydrating imidization method which uses a catalyst does not use a large amount of expensive auxiliary materials and is essentially an excellent economical method. The dehydrating reaction can occur merely by heating the maleamic acid in the presence of a solvent and the desired product maleimide is formed to some extent when heating is continued to remove the water of reaction from the reaction system. However, the rate of formation is too slow and impractical. Moreover, various unfavorable side reactions also occur and lead to lower selectivity. Accordingly, a catalyst is required for accelerating the dehydrating reaction and improving conversion and selectivity.

As a method using a catalyst, Japanese Patent Publication 51-40078 (1976) discloses a method for carrying out the imidization by dehydrating the maleamic acid in the presence of an acid catalyst and performing intramolecular cyclization by azeotropic distillation of the resulting water. The acid catalyst used are inorganic acids, such as sulfuric acid and phosphoric acid, and strong organic acids, such as p-toluenesulfonic acid having pka of 3 or less. Japanese Patent Publication 55-46394 (1980) described a method using a solvent system obtained by incorporation of an aprotic polar solvent with an azeotropic solvent in order to enhance the solubility of the maleamic acid. There are also known methods, such as Japanese Patent Laid-Open No. 60-11465 (1985), which use strong acid type ion exchange resin as an acid catalyst and a method for directly obtaining the maleimide by reacting maleic anhydride with primary amine in the presence of the strong acid catalyst mentioned above. Other methods employ the acid catalyst in combination with various additives. For example, Japanese Patent Publication 51-40078 (1976) carries out the reaction by the addition of a stabilizer such as a polymerization inhibitor and an alcohol in the presence of the acid catalyst. Japanese Patent Laid-Open Nos. 61-5066 (1986) and 62-63562 (1987) conduct the reaction in the presence of such a strong acid catalyst as sulfuric acid or phosphoric acid by incorporating one or more metal compounds of zinc, chromium, cobalt, nickel, iron, aluminum or palladium in a trace amount of 0.005 to 0.5%, preferably 0.01 to 0.1% by mole per mole of aniline.

Japanese Patent Laid-Open No. 61-60647 (1986) reacts maleic anhydride with a primary amine in an organic solvent to obtain a maleamic acid slurry and then intermittently or continuously charges the slurry to a second reaction vessel where the organic solvent is refluxing in the presence or absence of a catalyst. The catalyst is claimed as follows: "Suitable catalyst is oxyacid containing phosphorus or sulfur, or alkaline metal salt or alkaline earth metal salt thereof. In addition, salts, hydroxides, oxides and halides of the same metals (Ni. Co, Cu, Zn, Sn, Al, B, Sb, Li, Mg, Cr, Ti, V, Mn and Fe) as those of catalysts usually used for esterification, or montmorillonite catalyst can also be used as a catalyst." In the detailed specification disclosed as exemplary catalysts are many kinds of strong acids, and sodium salts and magunesium salts thereof. However, no description is given of a specific metal compound as a catalyst, but instead only the above claim is repeated Acid catalysts are used in the examples, but no example is disclosed which uses such a metal compound. Since the above patent has merely claimed many metal compounds, in addition to an acid catalyst, as a dehydrating imidization catalyst without any technical disclosure and, moreover, by misunderstanding as discussed hereafter, it is not recognized at all as so-called prior art in the aspect of metal-catalyzed reactions.

The common essential element for these known methods of catalytically dehydrating imidization is the use of an acid catalyst having strong Broensted acidity, i.e., a Broensted acid having pka 4 or less, for example, inorganic protic acids such as sulfuric acid, phosphoric acid, hydrobromic acid and fluorosulfonic acid, and organic protic acids, such as chloroacetic acid, fluoroacetic acid, trifluoromethanesulfonic acid, p-toluenesulfonic acid and sulfonic acid type ion exchange resins.

The process for preparing the N-substituted maleimide by catalytically conducting dehydrating imidization of the N-substituted maleamic acid is a direct reaction which does not consume auxiliary materials and hence is a substantially economical process. Accordingly, many acid catalyzed methods are known, as mentioned above. However, none is technically or economically satisfactory for the commercial production of N-substituted maleimides.

SUMMARY OF THE INVENTION

An object of the present invention is to provide a process for the preparation of a maleimide by a novel dehydrating imidization process which does not require the use of a strong acid catalyst.

Another object of the present invention is to provide a novel process which has substantially solved the important technical problems associated with the use of an acid catalyst, such as:

(1) poor selectivity or insufficient yield even though the above known inorganic or organic strong acid is used, (2) an inorganic acid or an expensive organic acid used for the catalyst in a large amount is poor in separating ability against an organic phase and hence is difficult to separate and recover after finishing the reaction, (3) the acid catalyst is apt to contaminate the reaction product and also has relatively low selectivity and hence leads to contaimination of the desired product with a large amount of by-products, which circumstances require complex purification procedures such as washing with water and separation in order to remove these impurities from the product, (4) the washing with water produces a large amount of waste water which must be treated before disposal, and (5) a strong acid catalyst used in a large amount at high temperatures requires anticorrosive materials for reactors and peripheral equipment, and hence leads to expensive production units.

An object of the invention is to solve these problems and to provide an economical large scale production process which can prepare an N-substituted maleimide from an N-substituted maleamic acid in high yield.

The process of this invention can economically prepare an N-substituted maleimide with high selectivity and in good yield from maleic anhydride or a derivative thereof and a corresponding primary amine or from the corresponding N-substituted maleamic acid.

A high purity maleimide which is particularly useful for a material of polymers can be readily produced on a large scale by the process of this invention.

The present invention relates to a process for the preparation of an N-substituted maleimide by heat-dehydrating an N-substituted maleamic acid in a solvent mixture containing an organic solvent capable of forming water azeotrope and an organic aprotic polar solvent and simultaneously conducting a dehydrating imidization reaction under azeotropic distillation of the reaction generated water, which comprises conducting the dehydrating imidization in the absence of a Broensted acid having a pKa of 3 or less and in the presence as reaction catalyst of catalytically effective amount of a zinc salt of the maleamic acid, metallic zinc, a zinc compound which forms a zinc salt of the maleamic acid in the reaction system, or mixtures thereof.

DETAILED DESCRIPTION OF THE INVENTION

The present inventors thought that, in order to substantially overcome the above problems, it was necessary to employ a different catalyst having high selectivity and serviceability in place of the conventional acid catalyst.

Initially, they intended to catalyze the reaction by incorporation of, for example, a zinc halide $ZnX_2$ into an organic weak acid exhibiting no catalytic activity, as follows:

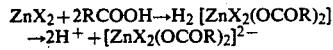
$$\rightarrow 2H^+ + [ZnX_2(OCOR)_2]^{2-}$$

wherein R—COOH is an organic carboxylic acid having a pKa above 3 such as acetic acid, and X is a halogen atom. A resulting zinc complex ion system could be expected to achieve a catalytic dehydrating imidization, because it would form a stronger Broensted acid than the applied carboxylic acid. The new catalyst system succeeded in promoting the reaction to give N-phenylmaleimide from N-phenylmaleamic acid in fairly high yield.

However, as a result of various experiments, the inventors found that an added carboxylic acid was spontaneously removed out of the reaction mixture together with azeotropic water generated by dehydration, and then the desired results for the reaction surprisingly could be obtained more advantageously merely by the addition of zinc halide alone in a catalytic amount to the reaction system without using the known strong acid catalyst mentioned above.

When the catalytic reaction of this invention was researched in further detail, the catalyst was found to exhibit extremely high activity and selectivity which could not be explained by the weak acid catalyst function of approximately pH 4 to 6 observed in the zinc complex ion system which presumably appeared from zinc halide and the maleamic acid as the organic carboxylic acid in the above reaction scheme. The phenomenon teaches that the mechanism of the catalytic reaction accelerated by the zinc compound is quite different from that of conventionally known acid catalysts. It is believed that the catalysis mechanism of the present invention is that the maleamic acid is subjected to coordination activation by some kind of active zinc complex, dehydrated and sterically tends to imidize by intramolecular cyclization.

When the reaction proceeds by the above mechanism of catalysis, zinc is considered to form a salt of maleamic acid as a precursor of active catalyst in the reaction mixture. For example, monomaleamic acid forms a zinc salt represented by the formula (IV):

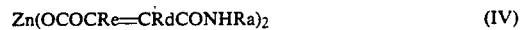

wherein HOCOCRe=CRdCONHRa is an N-substituted maleamic acid. Accordingly, zinc and its various compounds which can form the above salt has been broadly investigated.

As a result, other zinc salts, in addition to zinc halide, such as zinc carboxylate, zinc metal, zinc oxide, zinc hydroxide and zinc chelate have been found to exhibit excellent catalytic activity. On the other hand, no activity has been found for zinc sulfate and zinc phosphate. Metallic zinc and its compounds in the former group are comparable with respect to their catalytic properties with the inorganic salts in the latter group. The former group can form a zinc salt with the maleamic acid starting material whereas the latter group cannot form such a zinc salt. Consequently, it has been found that the catalytic activity of the selected zinc compound is dependent upon whether or not a zinc salt of the maleamic acid can be formed from metallic zinc or zinc compound under the reaction conditions or in the course of establishing the reaction conditions.

Because strong, e.g., pKa 3 or lower, Broensted acids interfere with or prevent the formation of the zinc salt of the maleamic acid or decompose the salt if added to the reaction mixture as the catalyst, the process of this invention is conducted in the absence of such strongly acidic compounds.

Further, a zinc salt of the maleamic acid has been isolated as new compound in the course of the reaction of this invention and the zinc salt has been identified as the precursor of the active catalyst. Then, some new zinc salts of maleamic acids have been synthesized by another preparative method, and the same dehydrating imidization reaction has been tried using a catalytic amount of the synthesized salt, with very excellent practical results which achieve the above objects obtained.

Additionally, it is worth noting that the dehydrating reaction has no induction period when zinc maleamate is used as the catalyst.

Refering to the addition of the metal compound in the presence of the strong acid catalyst, i.e., the description in the above Japanese Patent Laid-Open No. 61-5066 (1986), the amount for use is very small and the above catalytic action which is a characteristic of a zinc compound cannot effectively be exerted. For example, a catalytic effect is not observed even though zinc acetate is used in an amount of 0.05% by mole per mole of aniline in the preparation of N-phenylmaleimide as illustrated in comparative example 5. More importantly, a zinc salt of maleamic acid is difficult to form when the zinc compound is added in the presence of a strong acid. Consequently, the catalytic effect of a zinc compound cannot be achieved in the presence of the strong acid catalyst.

As to the metal compound used for the esterification catalyst in the above Japanese Patent Laid-Open No. 61-60647 (1986), most of these metal compounds, for example, Ni, Co, Cu, B, Mg, Cr, Mn and Fe, are inactive as catalysts for the reaction of this invention or exhibit no improvement in selectivity. Hence a common feature in catalysis cannot be found at all between the esterification reaction and the dehydrating imidization reaction of the present invention.

The N-substituted maleamic acid used as starting material for the process of this invention is an N-substituted monomaleamic acid, preferably one represented by formula (I):

Ra(NHCOCRd=CReCOOH)    (I)

wherein Ra is a monovalent radical, e.g., of an aliphatic, alicyclic or aromatic group of from 1 to 30 carbon atoms, and Rd and Re, which may be the same or different, are hydrogen atoms or monovalent substituents which are inactive under the reactions, or an N-substituted bis-and poly-maleamic acid represented by formula (II) or (III):

Rb(NHCOCRd=CReCOOH)$_2$    (II)

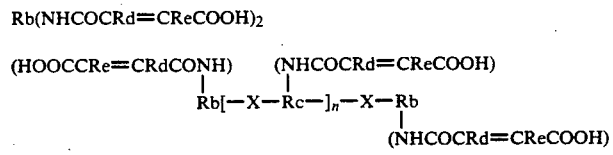    (III)

wherein Rb is a divalent radical, e.g., of an aliphatic, alicyclic or aromatic group having from 1 to 30 carbon atoms, Rc is a trivalent radical, e.g., of an aliphatic, alicyclic or aromatic group having from 1 to 30 carbon atoms, X is a divalent substituent which is inactive under the reaction conditions, and n is an integer of 0 to 50.

The starting N-substituted maleamic acids are compounds which can be readily obtained according to a known method in an almost theoretical yield by reacting a corresponding substituted or unsubstituted maleic anhydride with a primary mono-, di- or polyamine, preferably in a solvent.

Exemplary N-substituted maleamic acids include, for example, compounds wherein Ra in the formula is an aliphatic group, e.g., methyl, ethyl, n-propyl, i-propyl, n-butyl, sec-butyl, tert-butyl, amyl, i-amyl, hexyl, octyl, 2-ethylhexyl, dodecyl, octadecyl, or a corresponding unsaturated group, e.g., allyl, or a corresponding group bearing an aryl substituent, e.g., benzyl; an alicyclic group, e.g., as cyclopentyl and cyclohexyl; or an aromatic group, e.g., phenyl, naphthyl, or a corresponding group bearing 1,2 or more substituent, such as alkyl, halo, nitro, hydroxy, alkoxy, aryloxy, aryloyl, hydroxycarbonyl etc., e.g., tolyl, xylyl, styryl, dodecylphenyl, benzylphenyl, chlorophenyl, dichlorophenyl, hydroxyphenyl, methoxyphenyl, phenoxyphenyl, benzoylphenyl, carboxyphenyl and nitrophenyl. Also included are maleamic acid compounds wherein Ra has one or more substituents inactive in the reaction of this invention, for example, a halogen group, alkyl group, cycloalkyl group, aryl group, hydroxyl group, alkoxy group, aryloxy group, alkylmercapto group, nitro group, hydroxycarbonyl group, alkoxycarbonyl group, alkanoyl group, aryloyl group, nitrile group and a group containing monovalent substituents obtained by combining these groups.

Representative examples of Rd and Re substituents on the double bonded carbon atoms include, in addition to hydrogen atoms, the same monovalent substituents as described above for Ra.

Exemplary maleamic acids which are particularly useful in the process of this invention includes, for example, N-methylmaleamic acid, N-butylmaleamic acid, N-octylmaleamic acid, N-dodecylmaleamic acid, N-stearylmaleamic acid, N-cyclohexylmaleamic acid, N-phenylmaleamic acid, N-(o-tolyl)maleamic acid, N-dodecylphenylmaleamic acid, N-chlorophenylmaleamic acid, N-dichlorophenylmaleamic acid, N-(p-hydroxyphenyl)maleamic acid, N-(o- or p-methoxyphenyl)maleamic acid, N-(m-hydroxycarbonylphenyl)maleamic acid, and N-(m-nitrophenyl)maleamic acid.

Representative examples of N-substituted bis-and polymaleamic acid include, for example, compounds of formula (II) and (III) wherein Rb is divalent bridging group, e.g., aliphatic group, such as ethylene, tetramethylene and hexamethylene; an alicyclic group such as cyclohexylene and methylenebis(cyclohexylene); and an aromatic group such as phenylene, tolylene, xylylene, styrylene, dodecylphenylene, naphthylene, chlorophenylene, dichlorophenylene, hydroxyphenylene, methoxyphenylene, phenoxyphenylene, benzoylphenylene, carboxyphenylene and nitrophenylene. Rb also includes, as in the case of Ra, a group containing the above monovalent substituents which are inactive in the reaction.

X in formula (III) is a divalent substituent, including, for example, an alkylene groups, such as methylene, dimethylmethylene, cyclohexylmethylene, phenyl-methylene, ethylene, propylene, tetramethylene and hexamethylene; the same divalent alicyclic groups as Rb, e.g., cyclohexylene; divalent aromatic groups such as phenylene, tolylene and xylylene; ether groups; ketone groups; ester groups; amide groups; disulfide groups; sulfone groups; —O(C$_6$H$_4$)O—; —O(C$_6$H$_4$)CO(C$_6$H$_4$)O— and —O(C$_6$H$_4$)SO$_2$(C$_6$H$_4$)O—. These divalent substituents also include, as in the case of Ra, a group containing the above monovalent substituents which are inactive in the reaction.

Rc includes, for example, trivalent benzene ring substituents (C$_6$H$_3$) and also, as in the case of Ra, a group wherein hydrogen atoms are replaced with the above monovalent substituents which are inactive in the reaction. When n is zero in the formula (III), the formula indicates bis-maleamic acid. Wherein n is 1 or more, the formula indicates oligo- or polymaleamic acid.

Exemplary N-substituted bis-maleamic acids particularly useful for the practice of this invention include, for example,
N,N'-(m- or p-phenylene)bis-maleamic acid,
N,N'-(2,4-tolylene)bis-maleamic acid,
N,N'-(4,4'-diphenylmethane)bis-maleamic acid,
N,N'-(4,4'-diphenylether)bis-maleamic acid,
N,N'-(4,4'-diphenylketone)bis-maleamic acid,
N,N'-(4,4'-diphenyldisulfide)bis-maleamic acid and
N,N'-(4,4'-diphenylsulfone)bis-maleamic acid.

Additionally, N,N'-(4,4'-p-xylylenediphenyl)bis-maleamic acid having the structure wherein Rb is a phenylene group, X is xylylene group, Rd and Re are hydrogen atoms, and n is zero in formula (III), can also be used for the practice of the invention.

Particularly useful examples of N-substituted polymaleamic acid include, for example, polymethylenepolyphenylenepolymaleamic acid having the structure in the formula (III) [a polymeric homologue of N,N'-(4,4'-diphenylmethane)bis-maleamic acid] wherein Rb and Rc are benzene rings, X is a methylene group, Rd and Re are hydrogen atoms, and n is an integer of 1 to 10; and aromatic polymaleamic acid having the structure [a polymeric homologue of N,N'-(4,4'-p-xylylenediphenyl)bis-maleamic acid] wherein Rb and Rc are benzene rings, X is a xylylene group, Rd and Re are hydrogen atoms and n is an integer of 1 to 10.

In the process of the present invention a maleamic acid can be prepared in a solvent from maleic anhydride or its substituted derivative and a primary amine, and the dehydration reaction conducted using resultant maleamic acid as such without isolation.

The mole ratio of maleic anhydride to the amine group in the primary amine employed preferably is stoichiometric. However, it is often preferred to use a slight excess of maleamic acid, for example, in the range of about 1 to 1.1 by mole ratio. The excess maleic anhydride can be recovered after the reaction is complete and used again.

The catalyst for use in the process of the invention is one or more of zinc component selected from the group consisting of metallic zinc, a zinc salt of maleamic acid, and a zinc compound capable of forming said maleamic acid zinc salt in the reaction system.

The zinc salts of maleamic acid can be represented by the formula (IV) and (V):

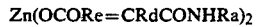  (IV)

  (V)

wherein Ra, Rd and Re are the same as in the starting maleamic acid, L is water of crystallization or an organic or inorganic neutral ligand, and m is an integer of 1 to 4.

The N-substituted maleamic acid used as a component of the catalyst may be the same as or different from that used as starting material for the dehydration reaction but preferably is the same. The ligand L is an organic or inorganic ligend capable of coordinating nonionic atoms such as nitrogen, oxygen and phosphorus to zinc. Exemplary ligands include, for example, amines, amides, alcohols, esters, ethers, phosphines, phosphites and water. Representative examples of preferred ligands are ligands of the polar solvents of this invention described below or the water of crystallization. The zinc salt of maleamic acid containing no ligand at all can also be used.

Although zinc salts of maleamic acid are very important as a precursor for the active catalyst, in the present invention, polymaleamic acid is also used as a starting material and hence the zinc salts are not limited to those represented by the formula (IV) and (V). Thus, the zinc salts useful in the catalyst can generally be defined as a compound represented by the formula (VI):

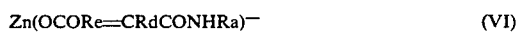  (VI)

wherein each zinc atom bears one or more maleamic acid groups.

Exemplary catalysts suitable for use in the process of the invention includes, for example, the zinc salt of N-methylmaleamic acid, N-butylmaleamic acid, N-dodecylmaleamic acid, N-stearylmaleamic acid, N-cyclohexylmaleamic acid, N-phenylmaleamic acid, N-tolylmaleamic acid, N-chlorophenylmaleamic acid, N-nitrophenymaleamic acid and N-hydroxyphenylmaleamic acid, and the corresponding zinc salt adduct obtained by coordinating water of crystallization or the neutral ligand to the zinc salt. Other examples are the zinc salt of
N,N'-(m- or p-phenylene)bis-maleamic acid,
N,N'-(2,4-tolylene)bis-maleamic acid,
N,N'-(4,4'-diphenylmethane)bis-maleamic acid,
N,N'-(4,4'-diphenylether)bis-maleamic acid,
N,N'(4,4'-p-xylylemediphenyl)bis-maleamic acid
and the a zinc salt adduct thereof similar to above.

Metallic zinc for use in the catalyst of the invention may be employed in any physical form, e.g., powder, granule, block, ribbons or film.

Further, various zinc compounds can be used for the in situ production of the catalyst which are capable of forming one the above described maleamic acid zinc salts in the reaction mixture. No particular limitation other than their ability to form a maleamic acid salts in situ, is imposed upon such zinc compounds, which include, for example, zinc halide, zinc salts of organic carboxylic acids, zinc oxide, zinc hydroxide, zinc chelates and other divalent zinc compounds.

Zinc halides include zinc chloride, zinc bromide, zinc iodide and zinc fluoride. Zinc chloride is preferably used. Zinc halide can also be used in combination with an organic carboxylic acid, providing the pKa of the combination is above 4. The organic carboxylic acid which is a secondary component of the catalyst is a monovalent or polyvalent carboxylic acid of aliphatic, alicyclic or aromatic group described below. The amount of acid used is from 0.1 to 5 moles per mole of zinc halide. Although an approximately stoichiometric amount is suitable, lesser amounts are also effective for accelerating the reaction and hence is prefered to commercial use.

The zinc halide and the organic carboxylic acid may be added separately to the reaction system or mixed prior to addition. The catalytic effect of the invention cannot be found at all when the organic carboxylic acid is singly used, as illustrated in comparative example 4.

Zinc oxide and zinc hydroxide may be used in any physical form, such as powder, granule, block or film. The zinc compounds are generally used singly and may be used as a mixture when necessary.

Zinc salts of carboxylic acids suitable for use as the catalyst include salts of weak monovalent and polyvalent aliphatic, alicyclic and aromatic carboxylic acids having a pKa above 3. Representative examples of carboxylic acids which may be used include, for example, formic acid, acetic acid, propionic acid, butyric acid, octanoic acid, lauric acid, stearic acid, glycine, lactic acid, oxalic acid, succinic acid, glutaric acid, adipic acid, azelaic acid, maleic acid, fumaric acid, citric acid, cyclohexylcarboxylic acid, naphthenic acid, benzoic acid, tolylic acid, chlorobenzoic acid, phthalic acid and terephthalic acid. Particularly preferred acids are formic acid, acetic acid, octanoic acid, stearic acid, benzoic acid and naphthenic acid. The zinc salt is generally used singly but may be used as a mixture when desired.

Zinc chelates which may be used as the catalyst include compounds of various chelating agents and zinc, including those containing one or more chelate bond composed of β-diketone. However, there is no restriction on the chelate compounds employed.

Examples of suitable β-diketones are those represented by the formula:

RfCOCHRgCORh wherein Rf, Rg and Rh each is a monovalent of an aliphatic, alicyclic or aromatic organic radical and Rg is a hydrogen atom or a halogen atom.

Exemplary β-diketones suitable for use include, for example, acetylacetone, dipivaloylmethane, 1,1,1-trifluoroacetylacetone, pivaloyl-1,1,1-trifluoroacetone, heptafluorobutanoylmethane, 1,1-dichloroacethylacetone, ethylacetoacetate, hexafluoroacetylacetone, 3-methylacetylacetone, 3-chloroacetylacetone, 3-bromoacetylacetone, cyclohexanoylacetone, benzoylacetone, 2-furoylacetone, 2-thenoylacetone, p-chlorobenzoylacetone, benzoyl-1,1,1-trifluoroacetone, β-naphthoyl-1,1,1-trifluoroacetone, 2-furoyl-1,1,1-trifluoroacetone, dibenzoylmethane, 2-furoylbenzoylmethane, 2-thenoylbenzoylmethane, 2-thenoyl-2-furoylmethane, bis(2-thenoyl)methane and 3-phenylacetylacetone.

Representative zinc chelate compounds which are preferably used as the catalyst include, zinc bis(acetylacetonate), zinc bis(dipivaloymethanate), zinc bis(1,1,1-trifluoroacetylacetonate), zinc bis(pivaloyl-1,1,1-trifluoroacetonate, zinc bis(ethylacetoacetate), zinc bis(benzoylacetonate), zinc bis(benzoyl-1,1,1-trifluoroacetate), zinc bis(dibenzoylmethanate), zinc bis(2-furoylbenzoylmethanate), and zinc bis(2-thenoyl-2-furoylmethanate). These catalysts are usually used singly but may be used as a mixture, if desired.

Zinc compounds in addition to those mentioned above, e.g., zinc nitrate and other organic zinc compounds, can also be used so long as they form a catalyst containing maleamic acid of the invention.

No particular limitation is placed upon the amount of the catalyst used but the amount is usually in the range of 0.1 to 20 mole % (0.001 to 0.2 gram atom of zinc), preferably in the range of 0.5 to 10 mole % (0.005 to 0.2 gram atom of zinc) per mole of the maleamic acid starting material.

Similar to the optimum quantity of the solvent in commercial use, the amount of catalyst used depends upon the starting material and the solvent used and the reaction conditions employed. However, zinc is generally a cheap material and hence it is economically favorable to use in an amount requiring no recovery. Known acid catalysts require recovery and reuse in view of the amount used. A complex washing step is also inevitable in processes using known acid catalysts due to accompanied contamination of the product. In contradistinction, the process of the present invention, which is the first process using zinc and/or its salt as the catalyst instead of an acid catalyst, is readily separated after finishing the reaction. Recovery and recycle of the catalyst is carried out with ease. The product can be readily purified and a complex post treatment is not necessarily required.

As can be seen by comparing the below described examples of this invention with the comparative examples, the catalyst of this invention inhibits side reactions, such as hydrolysis of cyclic imide, addition to double bonds between carbon atoms and polymerization, in addition to accelerating the dehydrating imidization reaction. Consequently, the catalyst performs the excellent function of improving the selectivity of the reaction.

An organic solvent capable of forming a water azeotrope is used in the present invention for removing water generated by the reaction by azeotropic distillation. The azeotropic solvent is one which forms a water azeotrope preferably in the temperature range from 50 to 200° C. and is inert under the reaction conditions. Suitable solvents include, for example, cyclohexane, benzene, toluene, ethylbenzene, xylenes, chlorobenzene, anisole, dichloroethane, diethoxyethane, cyclohexanone, methyl ethyl ketone and trioxane. The preferred solvents are the xylenes in view of their properties and cost.

The organic aprotic polar solvent is used for increasing the concentration of maleamic acid and the catalyst in the solution. Exemplary aprotic polar solvent suitable for the process of this invention include dimethylformamide, dimethylacetamide, dimethylsulfoxide, sulfolane, methylisobutylketone, γ-butyrolactone, hexamethylphosphoramide, N-methylpyrrolidone, tetramethylurea and 1,3-dimethyl-2-imidazolidinone. Prefered aprotic polar solvents are dimethylformamide, dimethylacetamide and dimethylsulfoxide.

These polar solvents generally decompose by heating in the presence of a strong acid and forms reactive acids and amines. Thus, a conventional dehydrating imidization process which uses an acid catalyst decomposes the polar solvent in the course of reaction and the decomposition products further increase by-products of the dehydrating imidization. On the other hand, the zinc catalyst of this invention can prevent decomposition of the polar solvent. It is a commercially important characteristic of the present invention that decomposition of solvent and accompanied decrease in the selectivity of maleimide production can be avoided.

The amount of the solvent mixture used is usually in an amount which provides a concentration of maleamic acid starting material therein to solvent in the range of 0.1 to 5 mole/l, preferably 0.5 to 3 mol/l. The content of polar solvent in the solvent mixture is usually in the range of 0.1 to 50% by volume and preferably in the range of 1 to 20% by volume. Optimum values of raw material concentration and solvent composition are dependent upon the starting material, catalyst, solvent and the reaction conditions such as catalyst amount, temperature and reaction time, employed.

Stabilizers such as known polymerization inhibitors may be added befor the dehydrating reaction or in the separation and purification step after the reaction is completed.

Exemplary stabilizers suitable for use include, for example, quinones such as hydroquinone, tert-butylhydroquinone and methoxybenzoquinone; phenols and bisphenols such as tert-butylcatechol and methoxyphenol; amines such as alkyldiphenylamine; sulfur compounds such as phenothiazine, mercaptobenzimidazol and methyleneblue; metal salts of dialkyldithiocarbamic acids such as copper dimethyldithiocarbamate and zinc dibutyldithiocarbamate; thiopropionic acid esters such as distearyl 3,3'-thiodipropionate; and phosphites such as triphenyl phosphite.

The reaction temperature employed is usually in the range of 50° to 250° C., and preferably is in the range of 80° to 160° C. In practice, optimum temperature depends upon the kind and composition of the above solvent mixture and concentration of the starting material. Although no particular restriction is imposed upon the reaction pressure, the reaction is preferably carried out under atmospheric pressure. Reaction time are usually in the range of 0.5 to 10 hours and preferably in the range of 1 to 5 hours, although optimum reaction time is practically determined on the basis of the selection of other reaction conditions.

The embodiments for preparing the maleimide from the maleamic acid by the process of the present invention will be illustrated below. The reaction can be carried out by batch, semicontinuous or continuous process.

Maleamic acid, the organic solvent for water azeotrope, organic aprotic polar solvent and the catalyst are mixed prior to reaction and charged to a reactor. Alternatively, maleamic acid and the catalyst are separately charged to the reactor together with the solvent respectively. The reactor is heated thereafter or in advance. The azeotropic solvent is heat-refluxed for a prescribed time and the generated water is simultaneously distilled out of the reactor as an azeotropic mixture. The reaction thus progresses and maleamic acid is converted to maleimide.

In the process of the invention, it is unnecessary to prepare the maleamic acid starting raw material separately. Preferably, maleic anhydride is dissolved in the above azeotropic solvent or the mixture thereof with the polar solvent and corresponding primary amine is added to the solution to prepare maleamic acid in situ. Then the catalyst is directly added to the maleamic acid solution or slurry thus obtained and the mixture is then refluxed to carry out the above azeotropic dehydration reaction. The maleamic acid can thus be prepared in an almost theoretical yield. Hence the latter process is usually more economical.

The reaction mixture thus obtained desirably is transferred to an evaporator to recover both solvents and then subjected to extraction, crystallization or distillation. The maleimide thus obtained has a purity of 90 to 100% and usually about 95 to 99.9%. The extraction residue, crystallization or distillation residue contain by-products and the catalyst in addition to a small amount of maleimide and unreacted maleamic acid. These residues can be returned to the reaction system for reuse as such or after suitable treatment. The zinc catalyst can also be separated by precipitation immediately after finishing the reaction or after separating the solvent, or by extracting from the solution.

The maleimide thus obtained can be readily converted to a high purity product suitable for practical application by usual purification methods such as extraction, crystallization, washing and distillation. Alternatively, maleimide can also be employed for commercial application as a solution in a suitable solvent when necessary.

The zinc metal base catalyst employed in the present invention exhibits no corrosivity, which behavior is markedly different from the conventional strong acid catalysts. Consequently, conventional and inexpensive materials can be used for the equipment and production units.

As mentioned above, the novel zinc catalyst employed in the present invention permits preparation of N-substituted maleimides, (1) in an extremely high selectivity and yield, (2) the catalyst can readily be separated, (3) without a complex purification step, such as washing with water, (4) without the expense of waste water disposal, and (5) using a reactor constructed with unexpensive conventional materials.

The present invention provides a process for economically preparing an N-substituted maleimide, in the presence of a high activity catalyst selected from the group consisting of a zinc salt of maleamic acid, metallic zinc and a zinc compound capable of forming said zinc salt of the maleamic acid in the reaction system, by using maleic anhydride or substituted derivative thereof and a corresponding primary amine as starting materials or by using an N-substituted maleamic acid as a raw material, in extremely high selectivity and yield, using simple separation and purification procedures.

The maleimides are useful for a material of various resins, agricultural chemicals and medicines. Particularly in recent years, they are utilized in large amounts for improving heat resistance of styrene base resin and the application to a comonomer for modifying other resins and a copolymer for polymer blend is now under development.

The invention will hereinafter illustrated further in detail by way of examples. However, it should of course be borne in mind that the subject matter and scope of this invention are not limited by these examples.

EXAMPLE 1

To a 300 ml flask equipped with a water separator, reflux condenser, stirrer and a thermometer, 15.44 g of maleic anhydride (hereinafter abbreviated as MAN), 70 ml of xylene (hereinafter abbreviated as Xy) and 10 ml of dimethylformamide (hereinafter abbreviated as DMF) were charged. A mixture of 13.97 g of aniline (hereinafter abbreviated as AN) and 20 ml of xylene was added with stirring at 80° C. at a constant rate over 15 minutes and further aged for 15 minutes to obtain N-phenylmaleamic acid as a white slurry. To the slurry, 2.04 g (2.5% by mole per mole of MAN) of zinc N-phenylmaleamate/dimethylformamide adduct (hereinafter abbreviated as $Zn(PMA)_2 \cdot DMF$) was added and the mixture was heated to reflux with stirring. Water generated by the reaction was removed by azeotropic distillation and the reaction was carried out at about 140° C. for 3.5 hours. The white slurry of PMA gradually dissolved as the dehydration reaction progressed and an orange yellow solution was obtained from which the catalyst component precipitated.

The solvent was recovered by evaporation under reduced pressure and the residue was extracted with hot cyclohexane. The extracted solution was successively concentrated to dryness to yield 22.31 g of extract, identified as N-phenylmaleimide (hereinafter abbreviated as PMI) by liquid chromatography, as yellow needles. The purity was 99.2% and content of PMA was almost zero. The 4.20 g of extraction residue contained 12.4% of PMI, 60.7% of PMA and 6.5% MAN.

The yields of PMI and PMA based on AN and selectivity of PMI based on PMA as an effective intermediate are summarized in Table 1, No. 1.

EXAMPLE 2

The procedure of Example 1 was employed except that twice by weight of the catalyst was used and the dehydration reaction was conducted for 2.5 hours. The results are illustrated in Table 1, No. 2.

EXAMPLE 3

The procedure of Example 1 was repeated except that 15.00 g of MAN and 2.38 g of the catalyst were used. The results are illustrated in Table 1, No. 3.

EXAMPLES 4 AND 5

The procedure of Example 1 was repeated except that ethylbenzene (abbreviated as PhEt in Table 1) and chlorobenzene (abbreviated as PhCl in Table 1) respectively were used instead of Xy. The results are illustrated in Table 1, No. 4 and No. 5.

EXAMPLE 6

The procedure of Example 1 was repeated except that 2.10 g of zinc N-phenylmaleamate/dimethylacetamide adduct (hereinafter abbreviated as $Zn(PMA)_2$.DMAC) as the catalyst and dimethylacetamide (hereinafter abbreviated as DMAC) in place of DMF were used and the dehydration reaction was conducted for 3 hours. The results are illustrated in Table 1, No. 6.

EXAMPLES 7 AND 8

The procedure of Example 1 was repeated except that 1.76 g of $Zn(PMA)_2$ as the catalyst was used, dimethyl sulfoxide (hereinafter abbraviated as DMSO) and N-methylpyrrolidone (hereinafter abbreviated as NMP) respectively were used as the solvent instead of DMF and the dehydrating reaction was conducted for 2.5 hours. The results are illustrated in Table 1, No. 7 and No. 8.

EXAMPLE 9

To the same type of the 500 ml reactor used in Example 1, 57.36 g of PMA, 180 ml of Xy, 20 ml of DMF and 4.66 g of $Zn(PMA)_2$.DMF as the catalyst were charged and heated to reflux. The reaction was carried out at about 140° C. for 3 hours by azeotropically distilling off the generated water. The white slurry of PMA gradually dissolved as the reaction progressed and an orange yellow solution was obtained from which the catalyst component precipitated. The reaction mixture was treated by the same procedures as carried out in Example 1. The results are illustrated in Table 1, No. 9.

EXAMPLE 10

The procedure of Example 1 was repeated except that 1.07 g of zinc chloride was used as the catalyst. The results are illustrated in Table 2. No. 10.

EXAMPLES 11-13

The procedure of Example 10 was repeated except that zinc bromide (Example 11), zinc iodide (Example 12) and zinc fluoride (Example 13) were respectively used as the catalyst in place of zinc chloride. The results are illustrated in Table 2, No. 11-13.

EXAMPLE 14

The procedure of Example 9 was repeated except that 1.23 g of zinc chloride was used as the catalyst and refluxing was carried out for 4 hours. The results obtained are illustrated in Table 2, No. 14.

EXAMPLE 15

The procedure of Example 10 was repeated except that 30.88 g of MAN, 27.94 g of AN and 2.15 g of zinc chloride catalyst were used. The results are illustrated in Table 2, No. 15.

EXAMPLE 16

The procedure of Example 10 was repeated except that 1.07 g of zinc chloride was used as the catalyst, 0.47 g of acetic acid was added and reflux was carried out for 3 hours. The results are illustrated in Table 2, No. 16.

EXAMPLES 17-21

The procedure of Example 16 was repeated except that zinc bromide and acetic acid (Example 17), zinc iodide and acetic acid (Example 18), zinc fluoride and acetic acid (Example 19), zinc chloride and formic acid (Example 20), and zinc chloride and propionic acid (Example 21) respectively were used as the catalyst in an amount of 5% by mole per mole of MAN in all cases. The results are illustrated in Table 2, No. 17-21.

EXAMPLE 22

The procedure of Example 14 was repeated except that 1.07 g of zinc chloride and 0.23 g of acetic acid were used as the catalyst and reflux was carried out for 3 hours. The results are illustrated in Table 2, No. 22.

EXAMPLE 23

The procedure of Example 1 was repeated except that 0.86 g of zinc acetate dihydrate (2.5% by mole per mole of MAN) was used as the catalyst. The results are illustrated in Table 3, No. 23.

EXAMPLE 24

The procedure of Example 23 was repeated except that 1.44 g (5.0% by mole per mole of MAN) of anhydrous zinc acetate was used and reflux was carried out for 135 minutes. The results are illustrated in Table 3, No. 24.

EXAMPLES 25-29

The procedure of Example 23 was repeated except that zinc formate (Example 25), zinc octanoate (Example 26), zinc stearate (Example 27), zinc naphthenate (Example 28) and zinc benzoate (Example 29) respectively were used as the catalyst in place of zinc acetate, and reflux was carried out for the time illustrated in Table 3. The results are illustrated in Table 3, No. 25-29.

EXAMPLE 30

The procedure of Example 9 was repeated except that 1.98 g of zinc acetate dihydrate was used as the catalyst. The results are illustrated in Table 3, No. 30.

EXAMPLE 31

The procedure of Example 1 was repeated except that 0.257 g (2.5% by mole per mole of MAN) of zinc powder was used as the catalyst and reflux was carried out for 3 hours. The results are illustrated in Table 3, No. 31.

EXAMPLE 32

The procedure of Example 31 was repeated except that 0.103 g (1.0% by mole per mole of MAN) of zinc powder was used as the catalyst and reflux was carried out for 3.5 hours. The results are illustrated in Table 3, No. 32.

EXAMPLE 33

The procedure of Example 31 was repeated except that 1.28 g of zinc oxide was used as the catalyst. The results are illustrated in Table 3, No. 33.

EXAMPLE 34

The procedure of Example 31 was repeated except that 0.391 g of zinc hydroxide was used as the catalyst and reflux was carried out for 3.5 hours. The results are illustrated in Table 3, No. 34.

EXAMPLE 35

The procedure of Example 9 was repeated except that 0.490 g of zinc powder was used as the catalyst. The results are illustrated in Table 3, No. 35.

EXAMPLE 36

The procedure of Example 1 was repeated except that 1.038 g (2.5% by mole per mole of MAN) of zinc bis(acetylacetonate) (hereinafter abbreviated as Zn(AA)$_2$ was used as the catalyst and reflux was carried out for 2.5 hours. The results are illustrated in Table 4, No. 36.

EXAMPLES 37-42

The procedure of Example 36 was repeated except that zinc bis(dipivaloylmethanate) (hereinafter abbreviated as Zn(DPM)$_2$) (Example 37), zinc bis(1,1,1-trifluoroacetylacetonate) (hereinafter abbreviated as Zn(TAA)$_2$) (Example 38), zinc bis(ethylacetoacetate) (hereinafter abbreviated as Zn(EAA)$_2$) (Example 39), zinc bis(benzoylacetonate) (hereinafter abbreviated as Zn(BA)$_2$) (Example 40), zinc bis(benzoyl-1,1,1-trifluoroacetonate) (hereinafter abbreviated as Zn(BFA)$_2$) (Example 41) and zinc bis(dibenzoylmethanate) (hereinafter abbreviated as Zn(DBM)$_2$) (Example 42) respectively were used as the catalyst in place of Zn(AA)$_2$ in an amount of 2.5% by mole per mole of MAN. The results are illustrated in Table 4, No. 37-42.

EXAMPLES 43 and 44

The procedure of Example 36 was repeated except that DMSO and NMP were respectively used in place of DMF as the polar solvent, 15.0 g of MAN was charged and reflux was carried out for 2 hours. The results are illustrated in Table 4, No. 43 and No. 44.

EXAMPLE 45

The procedure of Example 9 was repeated except that 1.977 g of Zn(AA)$_2$ was used as the catalyst and reflux was carried out for 2.5 hours. The results obtained are illustrated in Table 4, No. 45.

COMPARATIVE EXAMPLES 1-3

The procedure of Example 1 was repeated except without using the catalyst (Comparative Example 1), using 85% ortho-phosphoric acid as the catalyst in an amount of 5% by mole per mole of MAN(Comparative Example 2), or using 96% sulfuric acid as the catalyst in an amount of 5% by mole per mole of MAN(Comparative Example 3). The results are illustrated in Table 5, No. 1-3.

The effect of the catalyst in the present invention is clearly evident by comparing the results of the above examples with those of Comparative Example 1 with respect to yield and selectivity of PMI.

When the results of the examples are compared to the results of Comparative Examples 2 and 3, which are representative examples employing known acid catalysts, it is clearly observed that the catalyst of this invention is excellent with respect to the yield and particularly selectivity. In addition, the acid catalysts employed in the comparative examples generate extraordinary large amounts of by-products in the form of extraction residue, compared with the catalysts in the examples.

The catalyst of this invention is a zinc salt of the N-substituted maleamic acid and hence one can omit complex procedures such as washing with water, neutralization, separation and drying which are required for removing an acid catalyst from the reaction mixture. The effect is remarkable in view of practical application.

COMPARATIVE EXAMPLE 4

The procedure of Example 16 was repeated except that acetic acid alone was used in an amount of 5% by mole per mole of MAN in place of the catalyst composed of zinc chloride and acetic acid. The results are illustrated in Table 5, No. 4.

It is clear that addition of acetic acid alone exhibits no effect at all in the reaction.

COMPARATIVE EXAMPLE 5

The procedure of Example 23 was repeated except that 0.017 g of zinc acetate dihydrate (0.05% by mole per mole of MAN) was used as the catalyst. The results are illustrated in Table 5, No. 5.

A catalyst activity was not exhibited the zinc acetate because of the small amount used.

COMPARATIVE EXAMPLES 6-13

As mentioned above in detail, most of the same metal compounds as those of catalysts usually used for esterification can not be used as catalysts for the reaction of this invention. In order to confirm this, the procedure of Example 1 was repeated except that a cobalt compound (Comparative Example 6), a copper compound (Comparative Example 7), a magnesium compound (Comparative Example 8), a boron compound (Comparative Example 9), a nickel compound (Comparative Example 10), a chromium compound (Comparative Example 11), a manganese compound (Comparative Example 12) and an iron compound (Comparative Example 13) as illustrated in Table 5 were used. The results are illustrated in Table 5, No. 6-13.

Catalyst activity is not found in any of these comparative examples as clearly shown by comparing these results on the yield and selectivity of PM1 with those of Comparative Example 1 using no catalyst and those of Example 1 using the zinc catalyst.

EXAMPLE 46

To the same reactor used in Example 1, 15.44 g of MAN and 70 ml of Xy were charged. A mixture containing 16.3 g (0.15 mole) of p-aminophenol (hereinafter abbreviated as PAP), 65 ml of Xy and 15 ml of DMF was then added with stirring over 30 minutes at 80° C. and further aged for 15 minutes to prepare N-(p-hydroxyphenyl)maleamic acid as a white slurry.

Then, 0.865 g (3.0% by mole per mole of MAN) of anhydrous zinc acetate was added as the catalyst. The dehydration reaction was carried out under reflux with stirring at about 140° C. for 3 hours. Water generated in the reaction was distilled off as an azeotropic mixture.

After completing the reaction, the solvent was evaporated under reduced pressure and the thus-produced maleimide was extracted from the residue. The same procedure as conducted in Example 1 was repeated except that a mixture of cyclohexane and XY was used as extraction solvent in place of cyclohexane. The results of the identified product, N-p-Hydroxyphenyl)-maleimide are shown in Table 6. No. 46.

EXAMPLES 47-50

Substantially the same procedures as employed in Example 46 were carried out except that o-anisidine (Example 47) (abbreviated as MOAN in Table 6), p-chloroaniline (Example 48) (abbreviated as CLAN in Table 6), cyclohexylamine (Example 49) (obbreviated as CHA in Table 6) and dodecylamine (Example 50) (abbreviated as DODA in Table 6) respectively were used in place of PAP, and the catalyst and dehydration time as illustrated in Table 6 were used in the reaction.

The corresponding maleamic acids(abbreviated as MA in Table 6) and maleimides(abbreviated as MI in Table 6) could be obtained in all examples. The results are illustrated in Table 6, No. 47-50, in which $Zn(CHMAA)_2$ indicates zinc N-cyclohexylmaleamate.

EXAMPLES 51-54

Substantially the same procedures as employed in Example 46 were carried out except that p-phenylenediamine (Example 51) (abbreviated as PDA in Table 6), 2,4-tolylenediamine (Example 52) (abbreviated as TDA in Table 6), 4,4'-diamino-diphenylmethane (Example 53) (abbreviated as MDA in Table 6), and 4,4'-diamino-diphenyl ether (Example 54) (abbreviated as DADPE in Table 6) respectively were used in place of PAP in an amount of 0.075 mole in combination with 20 ml of DMF, and the catalyst and dehydration time as illustrated in Table 6 were used in the reaction. The corresponding bismaleimide was obtained. The results are summarized in Table 6, No. 51-54.

EXAMPLE 55

A polyamine mixture was used which has a composition represented by the following formula (IX):

$$(H_2N)-Rb-[-x-Rc(NH_2)-]n-X-Rb-(NH_2) \quad (IX)$$

wherein Rb is a phenylene group, Rc is a benzene ring, X is a p-xylylene group; and composed of 78% of 2,2'-bis(p-aminophenyl) xylylendiamine where n is zero, 18.5% of triamine where n is 1, and 6.5% of tetramine and higher amines where n is 2 and more (abbreviated as PAPX in Table 6).

Twenty grams of the polyamine mixture was used in place of PDA and the catalyst and dehydration time as illustrated in Table 6 were used in the reaction. Substantially the same procedures as employed in Example 51 were employed. A polymaleimide corresponding to the polyamine starting material was obtained. The results are illustrated in Table 6, No. 55.

TABLE 1

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 1 | $Zn(PMA)_2\cdot DMF$ | 2.5 | Xy | DMF | 210 | 99.2 | 87.5 | 8.9 | 96.0 |
| 2 | $Zn(PMA)_2\cdot DMF$ | 5.0 | Xy | DMF | 150 | 98.0 | 89.2 | 7.3 | 96.2 |
| 3 | $Zn(PMA)_2\cdot DMF$ | 3.0 | Xy | DMF | 210 | 95.4 | 84.4 | 6.7 | 90.5 |
| 4 | $Zn(PMA)_2\cdot DMF$ | 2.5 | PhEt | DMF | 210 | 94.5 | 78.5 | 13.5 | 90.8 |
| 5 | $Zn(PMA)_2\cdot DMF$ | 2.5 | PhCl | DMF | 210 | 97.0 | 85.5 | 9.0 | 94.0 |
| 6 | $Zn(PMA)_2\cdot DMAC$ | 2.5 | Xy | DMAC | 180 | 98.5 | 90.3 | 6.6 | 96.9 |
| 7 | $Zn(PMA)_2$ | 2.5 | Xy | DMSO | 150 | 95.2 | 84.5 | 6.1 | 90.0 |
| 8 | $Zn(PMA)_2$ | 2.5 | Xy | NMP | 150 | 94.0 | 79.0 | 9.4 | 87.2 |
| 9 | $Zn(PMA)_2\cdot DMF$ | 3.0 | Xy | DMF | 180 | 96.8 | 86.0 | 8.0 | 93.5 |

TABLE 2

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 10 | Zinc chloride | 5.0 | Xy | DMF | 210 | 95.1 | 77.3 | 10.3 | 86.2 |
| 11 | Zinc bromide | 5.0 | Xy | DMF | 210 | 96.1 | 73.4 | 13.6 | 85.0 |
| 12 | Zinc iodide | 5.0 | Xy | DMF | 210 | 97.1 | 73.3 | 15.8 | 87.1 |
| 13 | Zinc fluoride | 5.0 | Xy | DMF | 210 | 93.6 | 58.8 | 28.8 | 82.6 |
| 14 | Zinc chloride | 2.5 | Xy | DMF | 240 | 99.1 | 74.7 | 14.0 | 86.9 |
| 15 | Zinc chloride | 5.0 | Xy | DMF | 210 | 98.7 | 77.2 | 10.2 | 85.9 |
| 16 | Zinc chloride + Acetic acid | 5.0 | Xy | DMF | 180 | 97.5 | 78.5 | 8.5 | 85.8 |
| 17 | Zinc bromide + | 5.0 | Xy | DMF | 180 | 96.7 | 75.2 | 11.3 | 84.8 |

TABLE 2-continued

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 18 | Acetic acid Zinc iodide + Acetic acid | 5.0 | Xy | DMF | 180 | 98.1 | 75.5 | 12.8 | 86.6 |
| 19 | Zinc fluoride + Acetic acid | 5.0 | Xy | DMF | 180 | 94.0 | 62.1 | 25.1 | 82.9 |
| 20 | Zinc chloride + Formic acid | 5.0 | Xy | DMF | 180 | 95.8 | 77.6 | 8.2 | 84.5 |
| 21 | Zinc chloride + Propioni acid | 5.0 | Xy | DMF | 180 | 99.1 | 76.5 | 11.5 | 86.4 |
| 22 | Zinc chloride + Acetic acid | 3.0 | Xy | DMF | 180 | 99.1 | 74.7 | 14.0 | 86.9 |

TABLE 3

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 23 | Zinc acetate | 2.5 | Xy | DMF | 210 | 98.0 | 83.2 | 9.9 | 92.3 |
| 24 | Anhydrous zinc acetate | 5.0 | Xy | DMF | 135 | 96.2 | 87.8 | 5.5 | 92.9 |
| 25 | Zinc formate | 2.5 | Xy | DMF | 210 | 99.1 | 81.5 | 10.2 | 90.8 |
| 26 | Zinc octoate | 2.5 | Xy | DMF | 180 | 91.0 | 79.7 | 8.0 | 86.8 |
| 27 | Zinc stearate | 2.5 | Xy | DMF | 150 | 89.6 | 80.2 | 13.8 | 93.0 |
| 28 | Zinc naphthenate | 2.5 | Xy | DMF | 210 | 85.0 | 73.5 | 11.4 | 83.0 |
| 29 | Zinc benzoate | 2.5 | Xy | DMF | 150 | 92.8 | 82.5 | 9.4 | 91.1 |
| 30 | Zinc acetate | 3.0 | Xy | DMF | 180 | 99.0 | 82.0 | 9.4 | 90.5 |
| 31 | Zinc powder | 2.5 | Xy | DMF | 180 | 96.3 | 80.1 | 11.0 | 90.0 |
| 32 | Zinc powder | 1.0 | Xy | DMF | 210 | 91.7 | 58.6 | 28.5 | 82.5 |
| 33 | Zinc oxide | 10.0 | Xy | DMF | 180 | 96.6 | 89.7 | 4.0 | 93.4 |
| 34 | Zinc hydroxide | 2.5 | Xy | DMF | 210 | 92.6 | 42.8 | 47.1 | 80.9 |
| 35 | Zinc powder | 2.5 | Xy | DMF | 180 | 99.0 | 81.0 | 11.5 | 91.5 |

TABLE 4

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 36 | Zn(AA)$_2$ | 2.5 | Xy | DMF | 150 | 96.6 | 85.5 | 8.0 | 92.9 |
| 37 | Zn(DPM)$_2$ | 2.5 | Xy | DMF | 150 | 95.5 | 79.0 | 10.7 | 88.5 |
| 38 | Zn(TAA)$_2$ | 2.5 | Xy | DMF | 150 | 93.8 | 76.8 | 17.7 | 93.3 |
| 39 | Zn(EAA)$_2$ | 2.5 | Xy | DMF | 150 | 96.0 | 81.2 | 10.8 | 90.5 |
| 40 | Zn(BA)$_2$ | 2.5 | Xy | DMF | 150 | 99.1 | 80.5 | 7.7 | 87.2 |
| 41 | Zn(BFA)$_2$ | 2.5 | Xy | DMF | 150 | 95.8 | 75.0 | 16.8 | 90.1 |
| 42 | Zn(DBM)$_2$ | 2.5 | Xy | DMF | 150 | 97.0 | 77.1 | 13.9 | 89.5 |
| 43 | Zn(AA)$_2$ | 2.5 | Xy | DMSO | 120 | 91.8 | 81.2 | 9.5 | 89.7 |
| 44 | Zn(AA)$_2$ | 2.5 | Xy | NMF | 120 | 80.4 | 76.0 | 12.6 | 87.0 |
| 45 | Zn(AA)$_2$ | 2.5 | Xy | DMF | 150 | 99.0 | 82.5 | 9.3 | 91.0 |

TABLE 5

| No. | catalyst | concentration (mol %/MAN) | Azeotropic solvent | Polar solvent | Dehydration (min) | Purity PMI (%) | Yield PMI (%) | Yield PMA (%) | Selectivity PMI (%) |
|---|---|---|---|---|---|---|---|---|---|
| 1 | — | 0 | Xy | DMF | 210 | 90.8 | 18.0 | 64.5 | 50.7 |
| 2 | Orthophosphoric acid | 5.0 | Xy | DMF | 210 | 85.1 | 39.3 | 45.0 | 71.5 |
| 3 | Sulfuric acid (96%) | 5.0 | Xy | DMF | 120 | 92.6 | 72.9 | 8.4 | 79.6 |
| 4 | Acetic acid | 5.0 | Xy | DMF | 180 | 86.5 | 23.5 | 56.3 | 53.8 |
| 5 | Zinc acetate | 0.05 | Xy | DMF | 210 | 91.5 | 21.2 | 67.4 | 65.0 |
| 6 | Cobalt acetate | 2.5 | Xy | DMF | 210 | 88.0 | 16.2 | 78.3 | 74.6 |
| 7 | Copper acetate | 2.5 | Xy | DMF | 210 | 91.3 | 14.0 | 82.5 | 80.0 |
| 8 | Magnesium acetate | 2.5 | Xy | DMF | 210 | 90.8 | 18.8 | 74.1 | 72.8 |
| 9 | Boron oxide | 2.5 | Xy | DMF | 210 | 94.5 | 15.4 | 77.3 | 68.0 |
| 10 | Ni(AA)$_2$ | 2.5 | Xy | DMF | 210 | 89.2 | 19.9 | 64.2 | 55.6 |
| 11 | Cr(AA)$_2$ | 2.5 | Xy | DMF | 210 | 93.1 | 36.3 | 31.7 | 53.1 |
| 12 | Mn(AA)$_2$ | 2.5 | Xy | DMF | 210 | 90.5 | 16.2 | 63.7 | 44.6 |
| 13 | Fe(AA)$_2$ | 2.5 | Xy | DMF | 210 | 94.0 | 39.8 | 30.0 | 56.9 |

TABLE 6

| No. | Amine starting material | catalyst | concentration (mol %/MAN) | Dehydration (min) | Purity MI (%) | Yield MI (%) | Yield MA (%) | Selectivity MI (%) |
|---|---|---|---|---|---|---|---|---|
| 46 | PAP | Zinc acetate | 3.0 | 180 | 91.4 | 81.9 | 9.6 | 90.6 |
| 47 | MOAN | Zinc powder | 5.0 | 120 | 96.2 | 86.3 | 6.3 | 92.1 |
| 48 | CLAN | Zinc acetate | 5.0 | 210 | 90.5 | 83.5 | 8.2 | 91.0 |
| 49 | CHA | Zn(CHMAA)$_2$ | 5.0 | 210 | 97.5 | 85.0 | 8.1 | 92.5 |
| 50 | DODA | Zn(PMA)$_2$ | 5.0 | 180 | 95.5 | 80.8 | 10.3 | 90.7 |
| 51 | PDA | Zn(PMA)$_2$ | 3.0 | 210 | 93.2 | 75.5 | 14.2 | 88.0 |
| 52 | TDA | Zinc oxide | 5.0 | 210 | 97.0 | 79.0 | 12.7 | 90.5 |
| 53 | MDA | Zinc acetate | 3.0 | 180 | 93.5 | 82.1 | 11.0 | 92.3 |
| 54 | DADPE | Zn(AA)$_2$ | 3.0 | 120 | 96.3 | 77.3 | 13.6 | 89.5 |
| 55 | PAPX | Zn(AA)$_2$ | 3.0 | 180 | — | 87.0 | — | — |

What is claimed is:

1. In a process for the preparation of N-substituted maleimide by heat-dehydrating N-substituted maleamic acid in a solvent mixture containing an organic solvent capable of forming water azeotrope and an organic aprotic polar solvent and simultaneously conducting a dehydrating imidization reaction under azeotropic distillation of the reaction generated water, the improvement which comprises conducting the dehydrating imidization in the absence of a Broensted acid having a pKa of 3 or less and in the presence as reaction catalyst of a catalytically effective amount of a zinc salt of the maleamic acid, metallic zinc or a zinc compound which forms a zinc salt of the maleamic acid in the reaction system.

2. The process of claim 1 wherein the N-substituted maleamic acid is selected from the group consisting of N-methylmaleamic acid, N-butylmaleamic acid, N-octylmaleamic acid, N-dodecylmaleamic acid, N-stearylmaleamic acid, N-cyclohexylmaleamic acid, N-phenylmaleamic acid, N-(o-tolyl)maleamic acid, N-dodecylphenylmaleamic acid, N-chlorophenylmaleamic acid, N-dichlorophenylmaleamic acid, N-(p-hydroxyphenyl)maleamic acid, N-(o- or p-methoxyphenyl)maleamic acid, N-(m-hydroxycarbonylphenyl)maleamic acid and N-(m-nitrophenyl)maleamic acid.

3. The process of claim 1 wherein the N-substituted maleamic acid is selected from the group consisting of N,N'-(m- or p-phenylene)bis-maleamic acid, N,N'-(2,4-tolylene)bis-maleamic acid, N,N'-(4,4'-diphenylmethane)bis-maleamic acid, N,N'-(4,4'-diphenylether)bis-maleamic acid, N,N'-(4,4'-diphenylketone)bis-maleamic acid, N,N'-(4,4'-diphenyldisulfide)bis-maleamic acid, N,N'-(4,4'-diphenylsulfone)bis-maleamic acid, N,N-(4,4'-p-xylylenediphenyl)-bis-maleamic acid, and polymeric homologues thereof.

4. The process of claim 1 wherein the catalyst is selected from the group consisting of one or more of a zinc salt of N-substituted mono-, bis- and poly-maleamic acid and a zinc salt adduct obtained by coordinating water of crystallization or a neutral ligand to said zinc salt.

5. The process of claim 1 wherein the catalyst is one or more of the zinc salt of N-methylmaleamic acid, N-butyl-maleamic acid, N-dodecylmaleamic acid, N-stearylmaleamic acid, N-cyclohexylmaleamic acid, N-phenylmaleamic acid, N-tolylmaleamic acid, N,N'-(m- or p-phenylene)bis-maleamic acid, N,N'-(2,4-tolylene)-bis-maleamic acid, N,N'-(4,4'-diphenylmethane)bis-maleamic acid, N,N'-(4,4'-diphenylether)bis-maleamic acid, N,N'-(4,4'-p-xylylenediphenyl)bis-maleamic acid and a zinc salt adduct obtained by coordinating water of crystallization or a neutral ligand to said zinc salt.

6. The process of claim 1 wherein the catalyst is metallic zinc in powder, granule, block, ribbon or film form.

7. The process of claim 1 wherein the catalyst is a zinc halide.

8. The process of claim 1 wherein the catalyst is the reaction mixture of a zinc halide and weak organic carboxylic acid.

9. The process of claim 1 whrein catalyst is a zinc salt of a weak organic carboxylic acid.

10. The process of claim 8 wherein the zinc salt is zinc acetate.

11. The process of claim 1 wherein the catalyst is zinc oxide or zinc hydroxide.

12. The process of claim 1 wherein the catalyst is a zinc chelate.

13. The process of claim 11 wherein the catalyst is zinc acetylecetonate.

14. The process of claim 1 wherein the starting N-substituted maleamic acid is produced in situ by the reaction of the corresponding maleic anhydride and primary amine.

15. The process of claim 1 wherein the organic solvent capable of forming water azeatrope is one or more of cyclohexane, benzene, toluene, ethylbenzene, xylene, chlorobenzene, anisole, dichloroechane, diethoxyethane, cyclohexanone, methyl ethyl ketone and trioxane.

16. The process of claim 1 wherein the organic aprotic polar solvent is one or more of dimethylformamide, dimethylacetamide, dimethylsulfoxide, sulfolane, methyl isobutyl ketone, γ-butyrolactone, hexamethylphosphoramide N-methylpyrrolidone, tetramethylurea and 1,3-dimethyl-2-imidazolidinone.

17. The process of claim 1 wherein the organic solvent capable of forming water azeotrope is a xylene and the organic aprotic polar solvent is dimethylformamide.

18. The process of claim 1 wherein the solvent mixture contains from 0.1 to 50% by volume of the organic aprotic polar solvent.

19. The process of claim 1 wherein the concentration of the N-substituted maleamic acid in the reaction system is about 0.1 to 5 mol/l.

20. The process of claim 2 wherein N-substituted maleamic acid is produced in situ without isolation by the reaction of maleic anhydride with aniline.

21. The process of claim 1 wherein the reaction and the purification of the reaction product are conducted in the presence of a polymerization inhibitor.

22. The process of claim 1, wherein the N-substituted maleamic acid is produced in situ without isolation, at a concentration of 0.5 to 3 mole per liter, by the reaction of maleic anhydride with aniline in the solvent mixture of xylene and dimethylformamide containing from 1 to 30% by volume of the latter, and said acid is subjected in situ to dehydration imidization under azeotropic distillation of the reaction-generated water and in the presence of the catalyst of a zinc salt of said acid, metallic zinc, a zinc compound selected from the group consisting of zinc chloride, zinc acetate, zinc oxide, zinc hydroxide, zinc actylacetonate, and mixtures thereof, in an amount from 0.005 to 0.02 gram atom of zinc per mole of said acid, thereby producing N-phenylmaleimide.

23. The process of claim 1, wherein the N-substituted maleamic acid is N,N'-(4,4'-p-xylenediphenyl)bismaleamic acid.

* * * * *